(12) United States Patent
Mansi et al.

(10) Patent No.: US 10,068,669 B2
(45) Date of Patent: Sep. 4, 2018

(54) METHOD AND SYSTEM FOR INTERACTIVE COMPUTATION OF CARDIAC ELECTROMECHANICS

(71) Applicant: Siemens Healthcare GmbH, Erlangen (DE)

(72) Inventors: Tommaso Mansi, Plainsboro, NJ (US); Oliver Zettinig, Munich (DE); Bogdan Georgescu, Plainsboro, NJ (US); Ali Kamen, Skillman, NJ (US); Dorin Comaniciu, Princeton Junction, NJ (US); Saikiran Rapaka, Pennington, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 366 days.

(21) Appl. No.: 14/655,083

(22) PCT Filed: Jan. 20, 2014

(86) PCT No.: PCT/US2014/012164
§ 371 (c)(1),
(2) Date: Jun. 24, 2015

(87) PCT Pub. No.: WO2014/113746
PCT Pub. Date: Jul. 24, 2014

(65) Prior Publication Data
US 2015/0347709 A1    Dec. 3, 2015

Related U.S. Application Data

(60) Provisional application No. 61/754,174, filed on Jan. 18, 2013.

(51) Int. Cl.
*G06F 19/26*        (2011.01)
*G16H 50/50*        (2018.01)
(Continued)

(52) U.S. Cl.
CPC ............. *G16H 50/50* (2018.01); *G06F 19/00* (2013.01); *G06T 7/0012* (2013.01); *G06T 7/12* (2017.01);
(Continued)

(58) Field of Classification Search
None
See application file for complete search history.

(56) References Cited

U.S. PATENT DOCUMENTS

2013/0197881 A1* 8/2013 Mansi ................ G06F 17/5009
703/2
2013/0197884 A1* 8/2013 Mansi ..................... G06T 19/00
703/2

OTHER PUBLICATIONS

S Niederer et al. Simulating human cardiac electrophysiology on clinical time-scales. Frontiers in Physiology, Apr. 2011, vol. 2, Article 14, p. 1-7 (Year: 2011).*

(Continued)

*Primary Examiner* — John S Brusca
*Assistant Examiner* — Olivia M Wise

(57) ABSTRACT

A method and system for simulating cardiac function of a patient. A patient-specific anatomical model of at least a portion of the patient's heart is generated from medical image data. Cardiac electrophysiology potentials are calculated over a computational domain defined by the patient-specific anatomical model for each of a plurality of time steps using a patient-specific cardiac electrophysiology model. The electrophysiology potentials acting on a plurality of nodes of the computational domain are calculated in parallel for each time step. Biomechanical forces are calculated over the computational domain for each of the plurality of time steps using a cardiac biomechanical model coupled to the cardiac electrophysiology model. The biomechanical forces acting on a plurality of nodes of the computational domain are estimated in parallel for each time step. Blood (Continued)

flow and cardiac movement are computed at each of the plurality of time steps based on the calculated biomechanical forces.

26 Claims, 12 Drawing Sheets

(51) Int. Cl.
    *G06T 7/00*     (2017.01)
    *G06T 11/60*     (2006.01)
    *G06T 7/20*     (2017.01)
    *G06T 11/20*     (2006.01)
    *G06T 7/12*     (2017.01)
    *G06T 7/149*     (2017.01)
    *G06F 19/00*     (2018.01)

(52) U.S. Cl.
    CPC ............... *G06T 7/149* (2017.01); *G06T 7/20* (2013.01); *G06T 11/20* (2013.01); *G06T 11/60* (2013.01); *A61B 2576/023* (2013.01); *G06F 19/321* (2013.01); *G06T 2207/10088* (2013.01); *G06T 2207/20081* (2013.01); *G06T 2207/20124* (2013.01); *G06T 2207/30048* (2013.01); *G06T 2207/30104* (2013.01)

(56) References Cited

OTHER PUBLICATIONS

S. Rapaka et al. LBM-EP: Lattice-Boltzmann Method for Fast Cardiac Electrophysiology Simulation from 3D Images. Oct. 2012, In International Conference on Medical Image Computing and Computer-Assisted Intervention (pp. 33-40). Springer, Berlin, Heidelberg. (Year: 2012).*

ZA Taylor et al. High-Speed Nonlinear Finite Element Analysis for Surgical Simulation Using Graphics Processing Units. IEEE Transactions on Medical Imaging, May 2008, vol. 27, No. 5, pp. 650-663 (Year: 2008).*

PCT International Search Report dated Apr. 24, 2014 corresponding to PCT International Application No. PCT/US2014/012164 filed Jan. 20, 2014 (13 pages).

Pratt, Philip, et al; "Dynamic Guidance for Robotic Surgery Using Image-Constrained Biomechanical Models," Medical Image Computing and Computer-Assisted Intervention, Springer, Berlin, Heidelberg; pp. 77-85, XP019151689; 2010.

Sermesant, et al.; "An electromechanical model of the heart for image analysis and simulation", IEEE Transactions on Medical Imaging vol. 25, No. 5, pp. 612-625, XP001545798; 2006.

Mansi, et al; "Data-Driven Computational Models of Heart Anatomy, Mechanics and Hemodynamics: An Integrated Framework," Biomedical Imaging (ISBI), 2012 9th IEEE Int'l. Symposium, p. 1434, XP032199297; 2012.

Sermesant, M. et al; "Patient-Specific Electromechanical Models of the Heart for the Prediction of Pacing Acute Effects in CRT: A Preliminary Clinical Validation;" Medical Image Analysis, Oxford University Press, Oxford, GB, vol. 16, No. 1 XP028124532; 2011.

Aguado-Sierra, et al; "Patient-Specific Modeling of Dyssynchronous Heart Failure: A Case Study," Progress in Biophysics and Molecular Biology, vol. 107, No. 1, pp. 147-155, XP028309862; 2011.

* cited by examiner

METHOD AND SYSTEM FOR INTERACTIVE COMPUTATION OF CARDIAC ELECTROMECHANICS

This application claims the benefit of U.S. Provisional Application No. 61/754,174, filed Jan. 18, 2013, the disclosure of which is herein incorporated by reference.

BACKGROUND OF THE INVENTION

The present invention relates to modeling heart function using medical image data, and more particularly to an integrated framework to model heart anatomy, electrophysiology, biomechanics, and hemodynamics from clinical data and medical image data, which is fast enough to be interactive and embedded in a clinical setting.

Heart failure is a chronic disease with high social, economic, and healthcare impact, with an estimated two percent of adults in Western countries with the condition. Among the possible manifestations of heart failure, almost one third of all cases present dilated cardiomyopathy (DCM), which is characterized by a progressive enlargement and weakening of the heart. Treatment of DCM is challenging due to the large variability of etiologies (viral, genetic, ischemic) and the lack of predictors of disease prognosis. There is a need for computational tools that assist clinicians in predicting disease course and in planning treatment therapies.

BRIEF SUMMARY OF THE INVENTION

The present disclosure provides a method and system for patient-specific modeling of cardiac function. Embodiments of the present invention provide an integrated framework to model heart anatomy, electrophysiology, biomechanics, and hemodynamics from clinical information and medical imaging data, which is fast enough to be interactive and embedded in a clinical setting. Embodiments of the present invention utilize massively parallel architecture, such as a graphics processing unit (GPU), to implement an orthotropic model of myocardium tissue coupled with a near real-time cardiac electrophysiology model, efficient lumped models of cardiac hemodynamics, and data driven techniques for cardiac anatomy estimation from medical image data.

In one embodiment of the present invention, a patient-specific anatomical model of at least a portion of the patient's heart is generated from medical image data of the patient. Cardiac electrophysiology potentials of the patient is calculated over a computational domain defined by the patient-specific anatomical model for each of a plurality of time steps using a patient-specific cardiac electrophysiology model, wherein for each of the plurality of time steps, the electrophysiology potentials acting on a plurality of nodes of the computational domain are calculated in parallel. Biomechanical forces are calculated over the computational domain for each of the plurality of time steps using a cardiac biomechanical model coupled to the cardiac electrophysiology model, wherein for each of the plurality of time steps, the biomechanical forces acting on a plurality of nodes of the mesh domain are estimated in parallel. Blood flow and cardiac movement are computed at each of the plurality of time steps based on the estimated biomechanical forces. Computed electrophysiology potentials, biomechanical forces and cardiac parameters are displayed. User input is interactively received to change at least one of the parameters of at least one of the patient-specific anatomical model, cardiac electrophysiology model, and cardiac biomechanical model. The electrophysiology potentials, the biomechanical forces, and the blood flow and cardiac movement are recalculated.

These and other advantages of the invention will be apparent to those of ordinary skill in the art by reference to the following detailed description and the accompanying drawings.

DETAILED DESCRIPTION

The present invention relates to a method and system for interactive patient-specific modeling of cardiac function. Embodiments of the present invention are described herein to give a visual understanding of the patient-specific cardiac function and computation methodology. A digital image is often composed of digital representations of one or more objects (or shapes). The digital representation of an object is often described herein in terms of identifying and manipulating the objects. Such manipulations are virtual manipulations accomplished in the memory or other circuitry / hardware of a computer system. Accordingly, is to be understood that embodiments of the present invention may be performed within a computer system using data stored within the computer system.

Embodiments of the present invention provide an integrated framework to model heart anatomy, electrophysiology, biomechanics, and hemodynamics from clinical information and medical imaging data, which is fast enough to be interactive and embedded in a clinical setting. In particular, embodiments of the present invention utilize an efficient implementation on massively parallel architectures like multi-core CPU and graphics processing unit (GPU) of the cardiac electrophysiology model and the orthotropic Holzapfel-Ogden model of myocardium tissue coupled with efficient lumped models of cardiac hemodynamics and data driven techniques for cardiac anatomy estimation from medical image data.

Embodiments of the present invention provide methods for the computation of patient-specific cardiac models of cardiac function in a clinical setting. This requires robust image analytics to estimate cardiac anatomy from medical images and fast numerical methods to compute cardiac electromechanics for interactive use, parameter estimation and therapy planning. According to an advantageous embodiment of the present invention, an integrated but modular framework is disclosed for the computation of patient-specific cardiac electromechanics. This framework includes an integrated pipeline for anatomical model generation, a computationally efficient method to compute cardiac motion during any phase of the cardiac cycle, and in particular the isovolumetric phases, and a massively parallel framework to efficiently solve cardiac biomechanics and electrophysiology.

Figure 1:
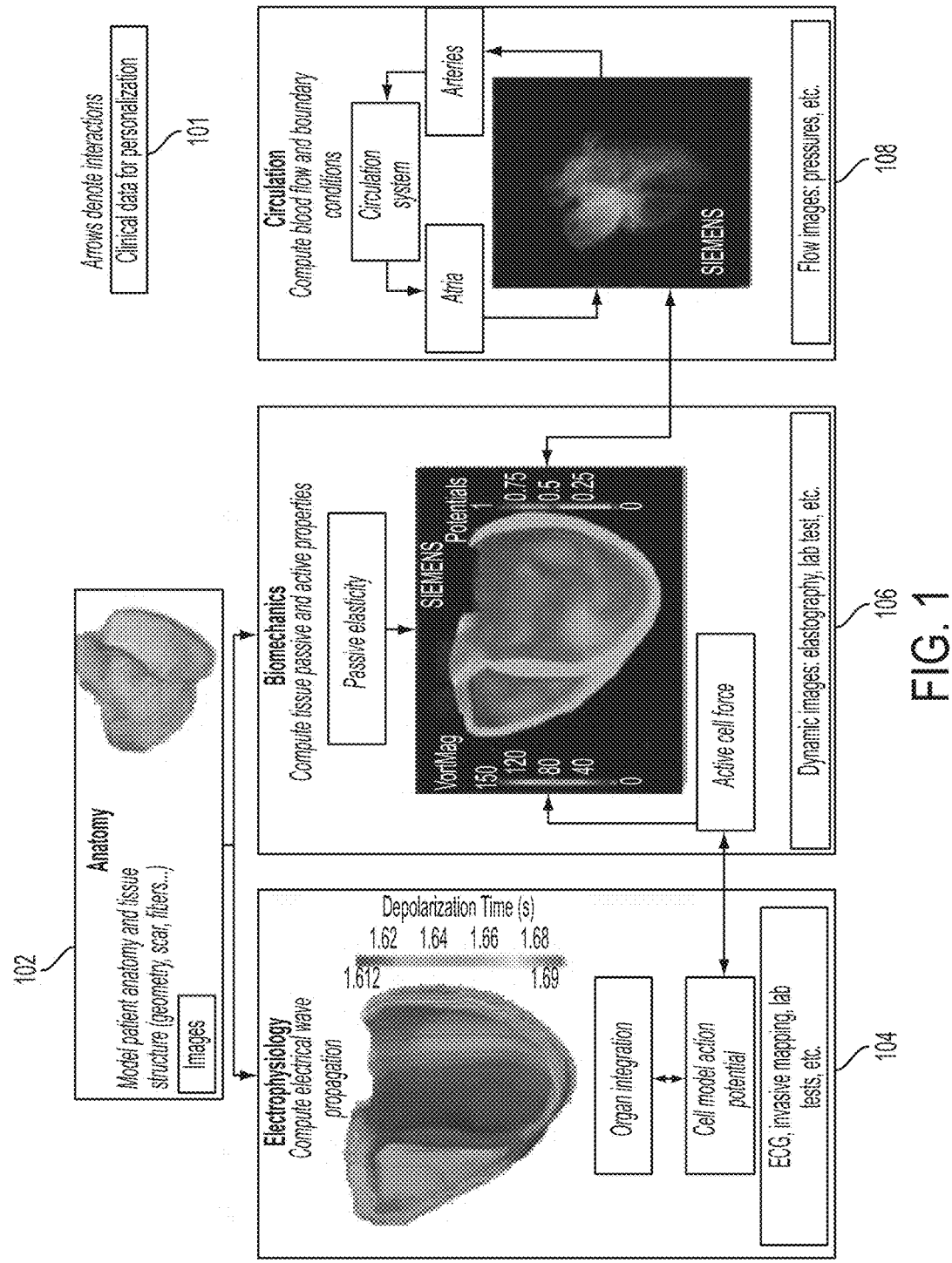
FIG. 1 illustrates an overview of a framework for patient-specific modeling of cardiac function according to an embodiment of the present invention.

FIG. 1 illustrates an overview of a framework for patient-specific modeling of cardiac function according to an embodiment of the present invention. As illustrated in FIG. 1, the framework for modeling cardiac function includes an anatomy model 102, an electrophysiology model 104, a biomechanics model 106, and a circulation model 108. Clinical data 101 of a patient is used for personalization of the models. The anatomy model 102 models patient anatomy and tissue structure, including cardiac geometry, scar tissue, and fiber structure. The electrophysiology model 104 computes the electrical wave propagation through the patient's cardiac anatomy, which is then weakly coupled to the biomechanics model 106, which computes tissue passive and active properties. The circulation model 108 employs a lumped model of cardiac hemodynamics to compute blood flow and boundary conditions of the biomechanics model 106.

Figure 2:
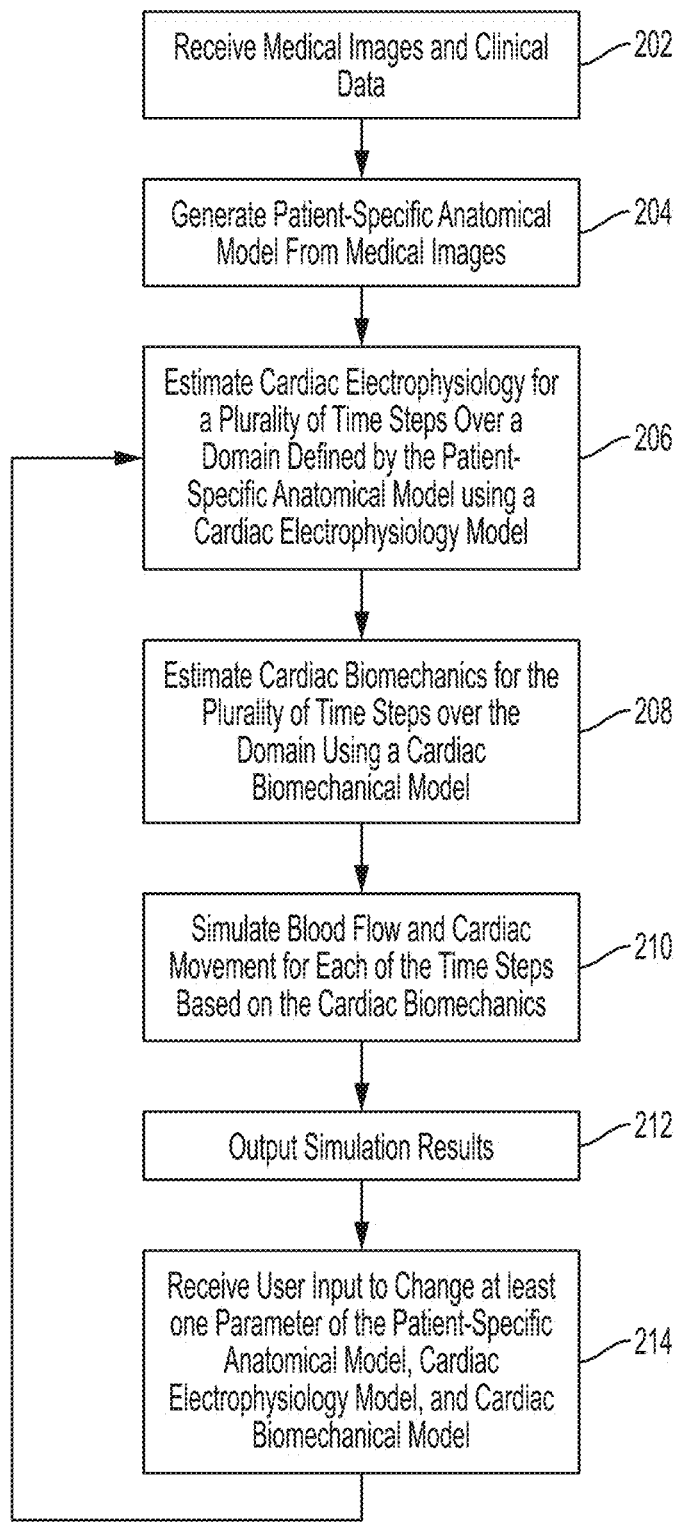
FIG. 2 illustrates a method for patient-specific modeling of cardiac function according to an embodiment of the present invention.

FIG. 2 illustrates a method for patient-specific modeling of cardiac function according to an embodiment of the present invention. As illustrated in FIG. 2, at step 202 medical images and clinical data of a patient are received. The medical images can be 3D preoperative images of the patient. The medical images may be a dynamic sequence of medical images acquired over at least one complete heart cycle or a static image. In advantageous embodiments of the present invention, the medical images can be magnetic resonance images (MRI) and/or computed tomography (CT) images and/or ultrasound images, but the present invention is not necessarily limited to these imaging modalities. The medical images may be received directly from a medical imaging device, such as an MR or ultrasound scanner, or the medical images may be received by loading stored medical images of a patient. The clinical data can include non-imaging patient-specific measurements, such as ECG, pressure measurements, etc. Pressure measurements may be acquired by catheter-based invasive pressure measurements or cuff pressure measurements.

At step 204, a patient-specific anatomical model of the heart is generated using the medical images. In one embodiment, heart morphology is automatically estimated, under expert guidance, from medical images, such as MRI, CT, or ultrasound, using a database-guided machined-learning framework. A mean shape model of the heart can be registered by automatically detecting its global position, orientation, and scale using Probabilistic Boosting Tree and Marginal Space Learning. An active shape model is then applied to refine the borders of the heart in the images. The detection algorithm results in three triangulations with point correspondences: left ventricle (LV), right ventricle (RV), and epicardium, which are then fused to form a closed surface of the biventricular myocardium. A tetrahedral volume is then generated and the facets are automatically tagged with the labels LV, RV, epi, LV septum, and RV septum according to the point-to-mesh distance between the volume mesh and the detected triangulations. A model of fiber and fiber sheets is generated using a rule-based calculation.

Figure 3:
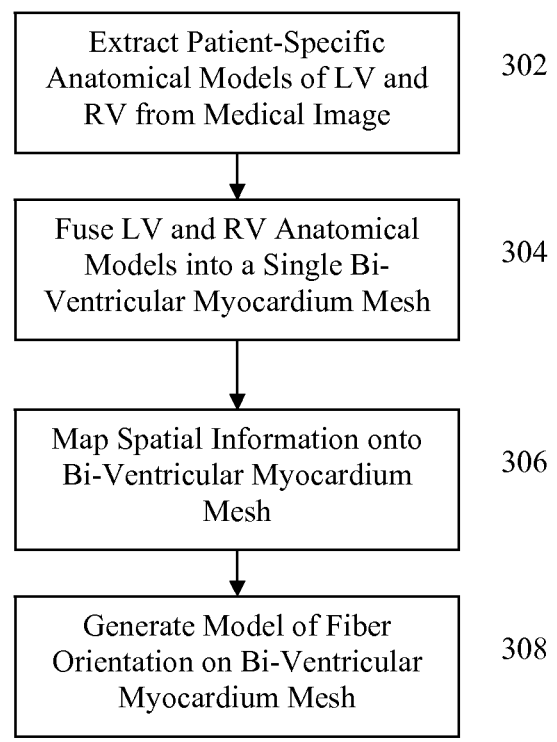
FIG. 3 illustrates a method for generating the patient-specific anatomical model of the left and right ventricles according to an embodiment of the present invention.
Figure 4:
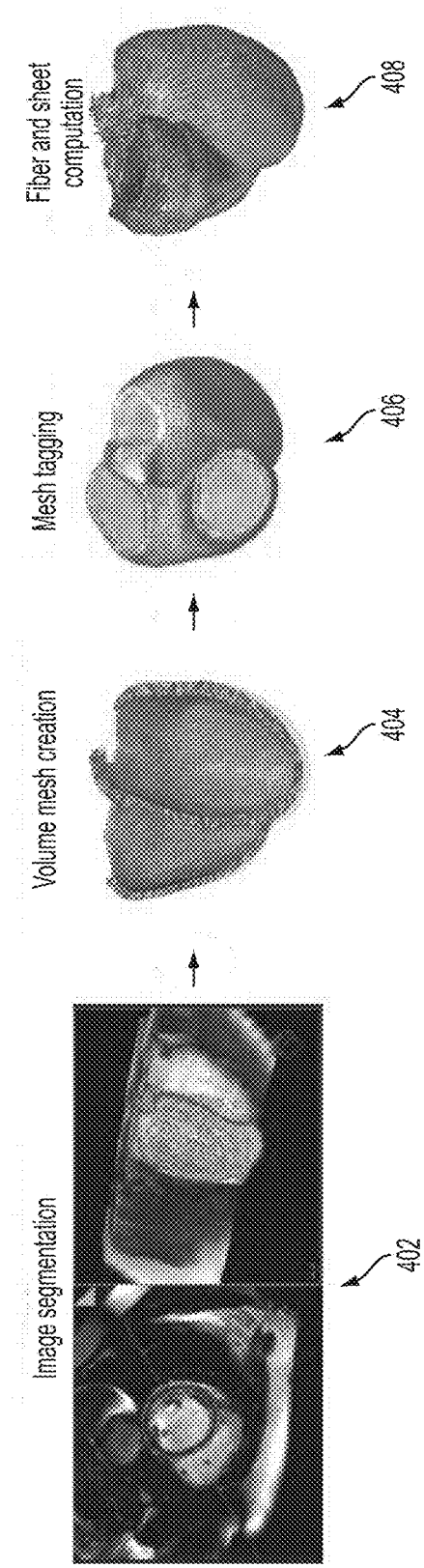
FIG. 4 illustrates exemplary results of the steps of FIG. 3.

FIG. 3 illustrates a method for generating the patient-specific anatomical model of the left and right ventricles according to an embodiment of the present invention. FIG. 4 illustrates exemplary results of the steps of FIG. 3. The method of FIG. 3 can be used to implement steps 204 of FIG. 2 in order to generate the patient-specific anatomical model. At step 302, anatomical models of the LV and RV are extracted from the medical images. In an advantageous embodiment, the LV and RV anatomical models show patient-specific heart morphology and dynamics, and are calculated automatically from medical images (MRI, CT, ultrasound, etc.). The LV and RV models can be detected in any preoperative images that cover the entirety of both cardiac ventricles. The LV and RV models can be extracted by segmenting the left endocardium, right endocardium, epicardium, and left and right outflow tract using a marginal space-learning based machine learning method. Obtained triangulations (meshes) are automatically labeled according to the anatomy they represent for subsequent processing.

For each of the LV and the RV, the heart chamber segmentation can be formulated as a two-step learning problem: anatomical structure localization and boundary delineation. In an advantageous embodiment, marginal space learning (MSL) can be used to apply machine learning to 3D object detection. The idea of MSL is not to learn a monolithic classifier directly in the full similarity transformation parameter space but to incrementally learn classifiers on marginal spaces. In particular, the detection of each heart chamber can be split into three problems: position estimation, position-orientation estimation, and position-orientation-scale estimation. A separate classifier is trained based on annotated training data for each of these estimation problems. The classifiers in the lower dimensional marginal spaces are used to prune the searching space efficiently. This object localization stage results in an estimated transformation (position, orientation, and scale) of the object (e.g., heart chamber).

After automatic object localization, the mean shape model of the object is aligned with the estimated transformation to get a rough estimate of the object shape. The shape is then deformed locally to fit the object boundary. Active shape models (ASM) can be used to deform an initial estimate of a non-rigid shape under the guidance of the image evidence and the shape prior. However, a non-learning based generic boundary detector, as used in conventional ASM applications, does not work effectively in heart chamber deformation due to the complex background and weak edges. Instead, a learning based boundary detector can be used to exploit more image evidences to achieve a robust boundary detection. Additional details regarding MSL-based heart chamber segmentation are described in U.S. Pat. No. 7,916,919, issued Mar. 29, 2011, and entitled "System and Method for Segmenting Chambers of a Heart in a Three Dimensional Image", United States Published Patent Application No. 2010/0040272, and United States Published Patent Application No. 2012/0022843, which are incorporated herein by reference. Image 402 of FIG. 4 shows exemplary results of segmenting the LV and RV models of step 302.

At step 304, the patient-specific LV and RV models are fused into a single bi-ventricular myocardium volumetric mesh. In a possible implementation, the LV and RV anatomies extracted can be fused together. The resulting closed surface is used to create a volumetric, tetrahedral mesh on which vertices are tagged into surface zones according to the underlying anatomy. Images 404 and 406 shows exemplary results of the volumetric mesh creation and the mesh tagging of step 304.

At step 306, spatial information is mapped onto the bi-ventricular myocardium mesh. Spatial information, such as scars, grey zones, and fibrosis can be identified in images, such as late delayed-enhancement MR images and mapped onto the bi-ventricular myocardium mesh. For example, scar locations and extent can be segmented in delayed-enhancement MR images using the method described in Dikici et al, "Quantification of Delayed Enhancement MR Images", In Proc. MICCAI 2004, LNCS 3216, pp 250-257, 2004, which is incorporated herein by reference. The scar information is mapped onto the bi-ventricular myocardium mesh by tagging the tetrahedral elements that lie within the segmented scar regions. This spatial information is important to simulate the electrical wave around scars, in particular for wave-reentry assessment, but also the impaired contractility due to dead tissue.

Figure 5:
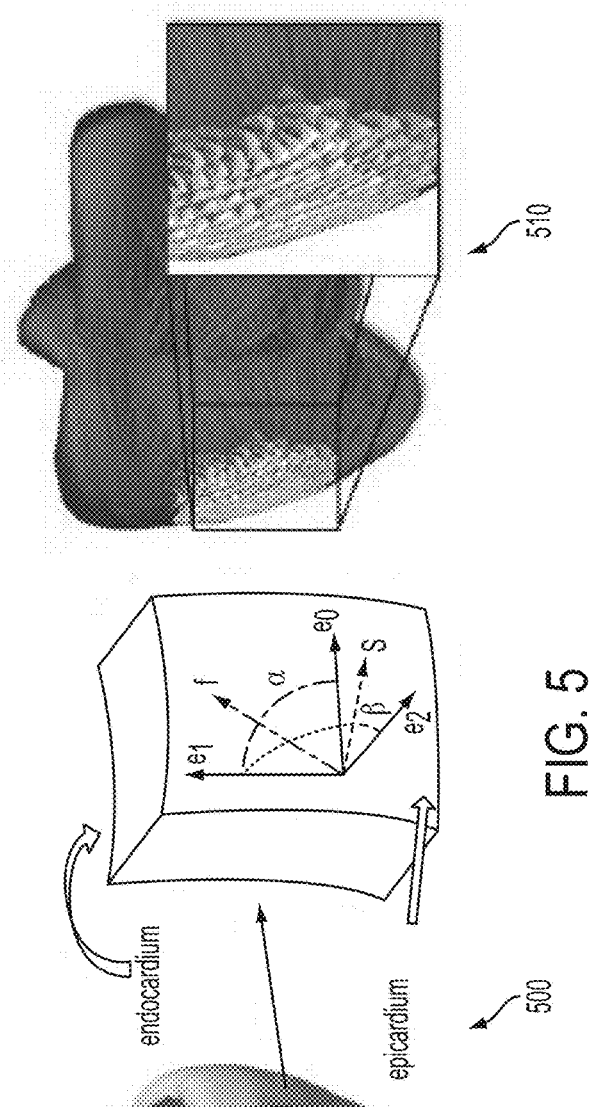
FIG. 5 illustrates the estimation of the fiber and fiber sheets using the rule based method.
Figure 5:
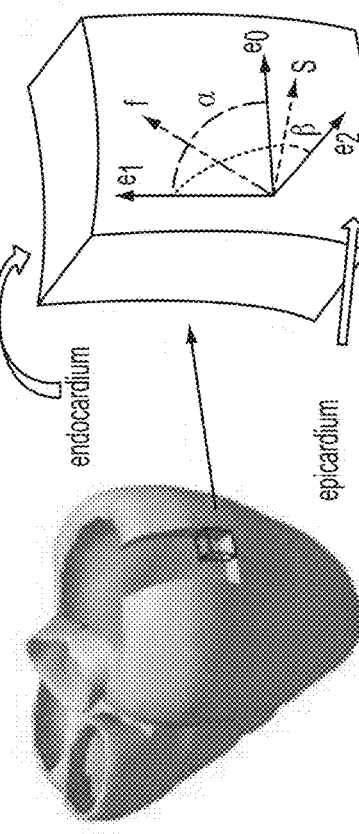

At step 308, model of fiber orientation is generated on the bi-ventricular myocardium mesh. In one embodiment, the model of fiber orientation may be computed directly from the anatomical model using a rule-based method. A generic model of myocardium fiber architecture that includes fiber and fiber sheets is computed. A rule-based strategy is followed to generate the fiber architecture to cover the entire bi-ventricular myocardium from apex to valves. Below the basal plane, which is identified automatically using point correspondences of the initial triangulations of the anatomical model, the fiber elevation angle $\alpha$, i.e. their angle with respect to the short axis plane, varies linearly across the myocardium, from −70 on the epicardium to +70 on the endocardium. Similarly, the sheet direction, which is defined by the angle $\beta$ with respect to the outward transmural axis, varies transmurally from +45 on the epicardium to −45 on the endocardium. $\alpha$ and $\beta$ are computed for each point of the volumetric bi-ventricular myocardium mesh between the apex and basal plane based on the geodesic distance to the endocardia and epicardia identified by the facet tags: $\alpha = (d_{epi}\alpha_{endo} + d_{endo}\alpha_{epi})/(d_{endo} + d_{epi})$, where $d_{epi}$, $d_{endo}$, $\alpha_{epi}$, and $\alpha_{endo}$ are the distances and angles at the endocardium and epicardium, respectively. The fiber and sheet orientations are then fixed around each valve. In particular, fibers are longitudinal around the aortic valve and tangential around the mitral, tricuspid, and pulmonary valves, and sheet normals are oriented towards the barycenter of the valves. The local orthonormal basis is then interpolated from the basal plane to the valve, first by following the myocardium surface, then throughout the myocardium thickness. For orthonormality preservation, the interpolation can be performed using a Log-Euclidean framework. Image 408 of FIG. 4 shows exemplary results of the fiber and fiber sheet estimation of step 308. FIG. 5 illustrates the estimation of the fiber and fiber sheets using the rule based method. As shown in FIG. 5, image 500 shows the definition of fiber directions f and sheet directions s in terms of the angles $\alpha$ and B ($e_0$ denotes the circumferential axis, $e_1$ denotes the longitudinal axis, and $e_2$ denotes the transmural axis). Image 510 shows the fiber and fiber sheet model estimated based on a patient-specific anatomy using the rule-based method.

In an alternative embodiment, in-vivo diffusion tensor (DT) MR images of the patient's cardiac fibers can be directly mapped to the anatomical model through image registration. In this case, the DT MR image is non-linearly registered to the medical image in which the LV and RV models are detected. The resulting transformation is used to deform the tensor field in the DT MR image towards the anatomical model. The Finite Strain method, the details of which are described in Peyrat et al., "A Computational Framework for the Statistical Analysis of Cardiac Diffusion Tensors: Application to a Small Database of Canine Hearts", IEEE TMI, 26(11):1500-1514, 2007, which is incorporated herein by reference, is used to reorient the tensors once the tensors are registered to the anatomical model.

Returning to FIG. 2, steps 206, 208, and 210 simulate cardiac function, including electrophysiology (step 206), biomechanics (step 208), and circulation (step 210) over a plurality of time steps using a mesh resulting from the patient-specific anatomical model generation of step 204 as a domain. The plurality of time steps can represent a complete cardiac cycle, a part of it, or several cardiac cycles. Parameters of the cardiac electrophysiology model, biomechanics model, and circulation model used in steps 206, 208, and 210 can be tuned based on the patient-specific anatomical model and the clinical data received for the patient in order to make the electrophysiology model, biomechanics, model, and circulation model patient-specific. In an advantageous implementation, patient-specific model parameters for the electrophysiology, biomechanics, and circulation models can be determined using the method described in United States Published Patent Application No. 2013/0197884, which is incorporated herein by reference in its entirety. According to an advantageous embodiment of the present invention, the electrophysiology computation in step 206 and the biomechanics computation in step 208 can each be performed using an efficient implementation that parallelizes the electrophysiology and biomechanical computations for the plurality of time steps. This efficient implementation can be executed in massively parallel architectures like GPU and is described in greater detail below.

At step 206, cardiac electrophysiology is calculated for a plurality of time steps over a domain defined by the patient-specific anatomical model using a cardiac electrophysiology model. In particular, the cardiac electrophysiology model calculates electrical wave propagation over the domain, resulting in an estimated action potential at each node of the domain for each time step. The patient-specific anatomical model can include meshes which show the cardiac anatomy at different cardiac phases. According to an advantageous implementation, a mesh representing a predetermined cardiac phase can be used as the domain for the electrophysiology estimate. For example, the mesh representing the cardiac anatomy at mid-diastasis can be used as the domain. The estimation of the cardiac electrophysiology for the plurality of time steps can be parallelized for efficient implementation using a massively parallel architecture (e.g. GPU), as described in greater detail below.

According to an embodiment of the present invention, a Mitchell-Scheffer mono-domain model of cardiac electrophysiology (EP) can be employed and solved using the recently proposed Lattice-Boltzmann LBM-EP method described in United States Published Patent Application No.

2013/0226542, which is incorporated herein by reference in its entirety. In particular, the dynamics of the normalized trans-membrane potential $v(t) \in [0,1]$ is governed by the coupled ordinary differential equations (ODE's) $\partial v/\partial t = h(t) v^2(1-v)/\tau_{in} - v/\tau_{out} + J_{stim} + c\nabla \cdot D\nabla v$ and $\partial h/\partial t = (1-h)/\tau_{open}$ if $v < v_{gate}$, $\partial h/\partial t = -h/\tau_{close}$ otherwise. In these equations, $J_{stim}$ is the stimulus current, c is the tissue diffusivity whose anisotropy is captured by the tensor D and $\tau_{in}$, $\tau_{out}$, $\tau_{open}$, $\tau_{close}$, and $v_{gate}$ are model parameters that control the shape of the action potential and the restitution curve. The LBM-EP method involves solving the system on a 3D Cartesian grid with 7-connectivity topology (6 edges+central position), on which a level-set representation of the patient-specific anatomy is constructed. Neumann boundary conditions are employed while stimulation currents are applied through Dirichlet boundary conditions at the septum. The model parameters are estimated to match the patient-specific clinical data measured for the patient.

At step 208, cardiac biomechanics are calculated for the plurality of time steps over the domain using a cardiac biomechanical model. In particular, the cardiac biomechanical model calculates various forces acting on the mesh nodes for each of the time steps. The cardiac biomechanical model is weakly coupled to the cardiac EP model, and the action potentials calculated for the mesh nodes for each of the time steps are used by the cardiac biomechanical model to calculate active stress forces. The estimation of the cardiac biomechanics for the plurality of time steps can be parallelized for efficient implementation using a massively parallel architecture, as described in greater detail below.

According to one embodiment, cardiac biomechanics are computed by solving the dynamics equation:

$$M\ddot{u} + C\dot{u} + Ku = F_a + F_p + F_b \quad (1)$$

where $\ddot{u}$, $\dot{u}$, and $u$ gather the accelerations, velocities, and displacements, respectively, of the mesh nodes, M is the mass matrix, K is the internal stiffness matrix, and C is the (Rayleigh) damping matrix. The force vectors $F_a$, $F_p$, and $F_c$ model active stress, ventricular pressure, and mechanical boundary conditions, respectively. The dynamics system is solved using the finite-element method on linear tetrahedral meshes and integrated over time with an Euler implicit scheme. The resulting linear system $\Xi u = F$ can be solved using the conjugate gradient method.

Passive Stress. The orthotropic Holzapfel-Ogden (HO) model can be used to compute tissue biomechanics. The strain-stress energy can be expressed as:

$$\Psi = \frac{a}{2b}\exp[b(I_1 - 3)] + \sum_{i=f,s} \mathcal{H}_s(I_{di}-1)\frac{a_i}{2b_i}\{\exp[b_i(I_{di}-1)^2]-1\} + \frac{a_{fs}}{2b_{fe}}[\exp(b_{fs}I_{sfs}^2)-1] + K(J-1)^2 \quad (2)$$

where the $a_k$'s and $b_k$'s are material constants, J is the Jacobian determinant of the deformation gradient F, J=det(F), K is a parameter equivalent to the bulk modulus, and the $I_k$'s are invariants of the right Cauchy-Green deformation tensor $C = F^T F$. In Equation (2), the subscripts f and s denote fiber and sheet directions, respectively. $\mathcal{H}_s(\cdot)$ is the logistic function, a smooth approximation of the Heaviside step functions employed herein for increased numerical stability.

For efficient computations, Equation (2) can be expressed according to the Multiplicative Jacobian Energy Decomposition (MJED) formulation. In particular, the energy function is written as $\Psi = \Sigma_k f^k(J) g^k(\tilde{I})$, where $\tilde{I} = [I_1, I_{4i}, I_{8fs}]$. The nodal force $F_i$ and the edge stiffness matrices $K_{ij}$ are then defined by $F_i = -(\partial \Psi/\partial x_i)^T$ and $K_{ij} = \partial^2 \Psi/(\partial x_i \partial x_j)$ where $x_i$ and $x_j$ are two connected nodes. Closed form expressions of $\partial f^k(J)/\partial x_i$, which do not involve calculating $C^{-1}$, are available. Deriving $g^k(\tilde{I})$ requires calculating their first and second derivative with respect to C, which can be easily calculated through the identities.

Active Stress. An active model can be used to calculate the active contraction force $F_a$. The active Cauchy stress tensor $\sigma_c$ is directly related to the action potential through the law $d\sigma_c(t)/dt + |u(t)| \cdot \sigma_c(t) = |u(t)|_+ \cdot \sigma_0$, where u(t) is the switch function $u(t) = k_{ATP}$ during depolarization, $u(t) = -k_{RS}$ during repolarization. $\sigma_0$ is the maximum asymptotic stress and $|u(t)|_+$ is the positive part of the switch function. The depolarization and repolarization times are obtained from the cardiac EP model.

Mechanical Boundary Conditions. Two mechanical boundary conditions are considered, $F_b = F_{base} + F_{pc}$. First, the effect of arteries and atria on ventricular motion is modeled by connecting the valve plane vertices to springs with anisotropic stiffness such that radial motion is permitted. The fixed extremity of the springs corresponds to the rest position of the nodes taken at mid-diastasis. The contributions of the springs are gathered into the force vector $F_{base}$. The heart motion is also constrained inside the pericardium bag and by the neighboring lungs and liver. These interactions are modeled using a contact-based pericardium constraint. In particular, let $\delta\Omega$ be the pericardium, defined by the epicardium of the patient-specific anatomical model at end diastole. A distance map $D_{\delta\Omega}$ is computed from $\delta\Omega$ with $D_{\delta\Omega} < 0$ inside the pericardial bag. The force $F_{pc}(x) = kVD_{\delta\Omega}(x)(D_{\delta\Omega}(x)-\Delta)^2/((D_{\delta\Omega}(x)-\Delta)^2+m^2)$ is then added to the epicardial nodes when $D_{\delta\Omega}(x) > \Delta$. The parameters A (dilation parameter of the pericardium bag), k (contact force amplitude), and m (contact force rate) control where the force starts to apply, the maximum strength of the force, and how fast the maximum strength is reached.

Returning to FIG. 2, at step 210, blood flow and cardiac movement are computed for each of the time steps based on the estimated cardiac biomechanics. The blood flow, or hemodynamics, is simulated using a cardiac circulation model and the cardiac movement is simulated based on the cardiac biomechanics estimated in step 208. The simulated blood flow and cardiac movement provides boundary conditions for the cardiac biomechanical model. That is the simulated blood flow and cardiac movement at one time step provides boundary conditions for the cardiac biomechanics estimation for the next time step.

Cardiac Cycle. The four cardiac phases (filling, isovolumetric contraction, ejection, and isovolumetric relaxation) are calculated by alternating the boundary conditions on the endocardia. Let q be the ventricular flow defines as the time derivative of the ventricular cavity volume. During filling (q>0), ventricular pressure is set equal to the atrial pressure, which is computed using a time-varying elastance model. As soon as the flow is reverted as an effect of myocardium contraction, the atrio-ventricular valve closes and the isovolumetric constraint described below is enabled. When the ventricular blood pressure reaches the arterial pressure, the arterial valve is opened and blood is ejected. The arterial pressure, calculated using a 3-element Windkessel model, is applied to the endocardium. An accordant pattern of phase selection and pressure application is used for the second half of the heart cycle. Ventricular pressure is added to the dynamics system using the nodal forces $F_p = pN$, where p is the pressure and N is a vector gathering lumped areas vectors ndS of the endocardial surface.

Efficient Isovolumetric Constraint. To keep the ventricular volume V constant during isovolumetric phases, an efficient projection-prediction method can be used that estimates the pressure $\tilde{p}(t)$ which ensures that $V(t+dt)=V_0$, where dt is the time step. To this end, the dynamic system is first solved without constraint, computing unconstrained new vertex positions $\hat{x}(t+dt)$. Thereafter, the system is reformulated including an unknown corrective pressure $\lambda(t)$: $\Xi(x(t+dt)-x_0)=F+\lambda N$. Solving the system at t+dt yields $(x(t+dt)-x_0)=(\hat{x}(t+dt)-x_0)+\lambda\Xi^{-1}N$. The constrained system thus can be expressed as:

$$\begin{cases} x(t+dt) = \hat{x}(t+dt) + \lambda(t)\Xi^{-1}N \\ V(t+dt) = V_0 \end{cases} \quad (3)$$

The Lagrangian coefficient $\lambda$ is computed by solving a third-order polynomial. The vertices are then projected by applying the respective displacements. The corrected pressure $\tilde{p}(t)=p(t)+\lambda(t)$ is then computed and the pressure at the next time step is predicted by utilizing a second-order Taylor expansion scheme, $p(t+dt)=\tilde{p}(t)+dt d\tilde{p}/dt+dt^2 0.5 d^2\tilde{p}/dt^2$, which permits more accurate pressure curves and phase switches.

Fast Massively Parallel Implementation

According to an advantageous embodiment of the present invention, since the computational limitations of the above described computational model of cardiac function are predominantly present in the electrophysiological and biomechanical models, these components can be parallelized in order to be implemented on a massively parallel architecture like a GPU.

Solving the dynamics equation of Equation (1) using finite element method (FEM) involves computing nodal forces that are calculated by accumulating the contributions of all elements sharing each mesh node. For example, calculating of the nodal pressure force requires accumulating the contribution of surrounding triangles while calculating the nodal passive stiffness requires accumulating the contribution of surrounding tetrahedron edges. According to an embodiment of the present invention, a parallel implementation strategy, which avoids the racing condition that may emerge when different kernels write at the same shared memory during accumulation, is utilized.

Figure 6:
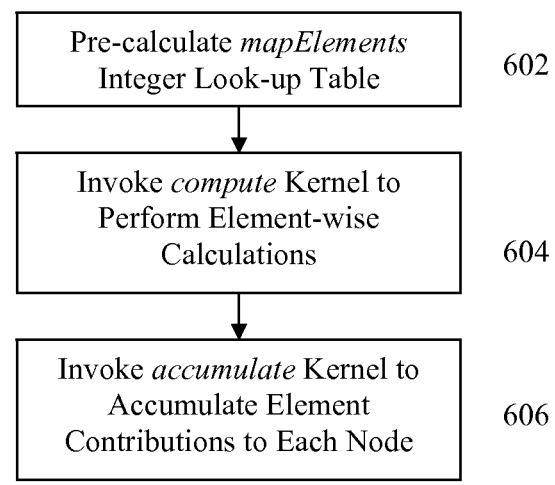
FIG. 6 illustrates a generalized parallel implementation method according to an embodiment of the present invention.

FIG. 6 illustrates a generalized parallel implementation method according to an embodiment of the present invention. Referring to FIG. 6, at step 602, an integer look-up table, mapElements, is pre-calculated at the beginning of the simulation. mapElements is stored in a texture map for increased efficiency. Let V be the maximum valence of the mesh (i.e., the maximum number of elements connected to a node), and $N_n$ the number of nodes. mapElements is a table of size $2 \times N_n \times V$ that stores for any given node i the pairs (j,k), where j is the index of each adjacent element and k is the local index of that node in that element (e.g., $k \in [1,4]$ if the element is a tetrahedron). Remaining positions, which occur when the node is shared by less than V elements, are initialized with a negative value.

At step 604, a kernel compute is invoked across the $N_e$ elements to perform the element-wise calculations. The compute kernel stores the element-wise contributions into separate floating point textures $T^k$ of size $N_e$ each. There are as many textures $T^k$ as nodes shared by each element. For example, there are three textures $T^k$ for triangle elements and four textures $T^k$ for tetrahedral elements.

At step 606, a kernel accumulate is invoked across $N_n$ threads to accumulate the element contributions to each node. This is achieved by looping over all V pairs (j,k) corresponding to each respective node in the mapElements look-up table, and accumulating the contributions stored at the j-th positions of textures $T^k$ to the nodal force.

According to an advantageous embodiment, the look-up texture map mapElements only requires the maximum valence, and not the actual valence for a given node (which is not constant). Accordingly, only one texture needs to be managed instead of two, resulting in simpler code, and also resulting in additions speed-up through texture alignment with the accumulate kernel threads. The higher memory demand is negligible in light of current GPU memory sizes. For a mesh with $N_e$ elements, an average tetrahedron/vertex valence of $V_{avg}$ and a maximum valence of $V_{max}$, $(v_{max}/V_{avg})$-fold more device memory needs to be allocated, in total amounting to $8NV_{max}$ bytes.

Figure 7:
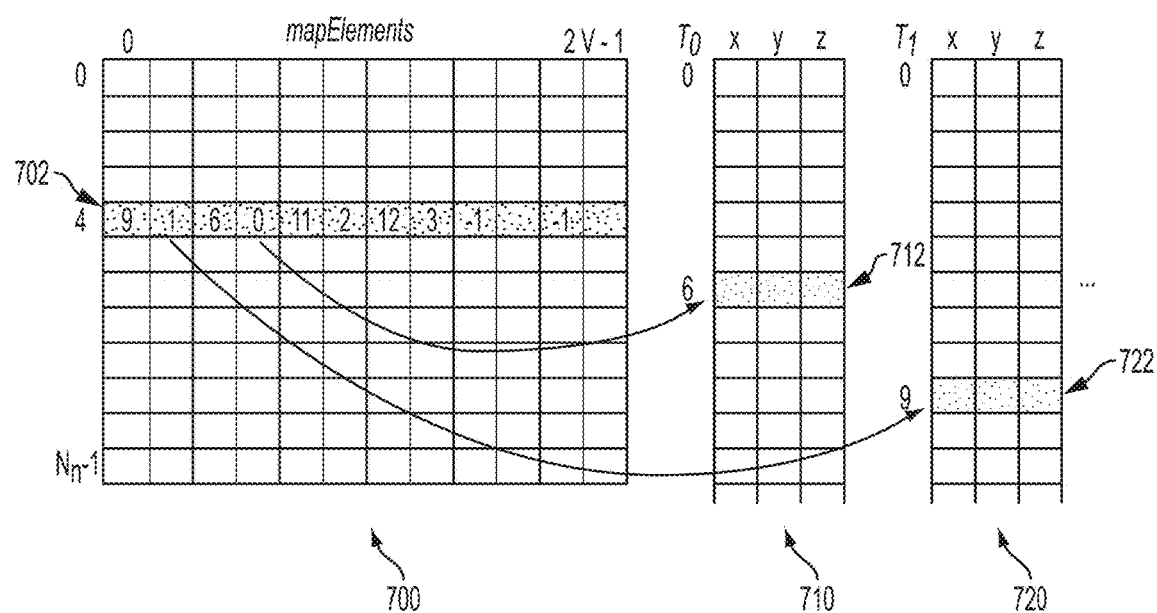
FIG. 7 illustrates an example of determining element contributions to a node using a mapElements look-up table according to an embodiment of the present invention.

FIG. 7 illustrates an example of determining element contributions to a node using a mapElements look-up table according to an embodiment of the present invention. As shown in FIG. 7, mapElements table 700 shows an entry 702 for vertex number 4. While the maximum valence is set to six, vertex number 4 is shared by four elements (9, 6, 11, and 12). Vertex number 4 is the node 1 for element 9, node 0 for element 6, node 2 for element 11, and node 3 for element 12. The contribution of each element to each respective node number is stored by the kernel compute in a different texture $T_i$, of which only the first two are shown in FIG. 7. The kernel accumulate gathers and accumulates the contributions of each element for a particular node. As shown in FIG. 7, for vertex number 4, the accumulate kernel accumulates the entry 712 corresponding to element 6 in texture $T_0$ 710 and the entry 722 corresponding to element 9 in texture $T_1$ 720. Similarly, the accumulate kernel also gathers the entry corresponding to the element 11 in texture $T_2$ (not shown) and the entry corresponding to element number 12 in $T_3$ (not shown).

Passive Stress. The implementation of the HO model described herein is formulated in a total Lagrangian framework, allowing for the pre-computation of variables and the parallel execution for nearly all calculations. From the rest state, tetrahedron shape vectors $D_i$ are calculated as the cross product of two opposing edges respectively, and the tensors of fiber sheet, and cross-sheet directions ((f⊗f, s⊗s, f⊗s+s+s ⊗f). At each time step, the deformation gradient F can be expressed as $\Sigma_{i=0}^{4} x_i D_i$, such that the right Cauchy-Green deformation tensor C and the invariants $I_1$, $I_{4i}$, $I_{8fs}$ can be calculated. For the derivative of the Jacobian determinant J, the formula $J = \frac{1}{6} V_0 e_{30}(e_{10} \times e_{20})$, where $e_{ij}$ is the edge $x_i - x_j$, is utilized to get a closed form. By using the definitions defined above in connection with step 208 of FIG. 2 and the parallelization method illustrated in FIG. 6, the forces (tetrahedron/vertex look-up table) and the edge stiffness matrices (tetrahedron/edge look-up table) can be calculated as required by the implicit integration scheme.

Other Components. The parallelization method of FIG. 6 can also be applied to perform fast computation of the active stress (tetrahedron/vertex look-up table) and ventricular pressure forces (endocardial triangle/vertex look-up table).

LBM-EP. Since the Lattice-Boltzmann methods for computing cardiac electrophysiology are inherently node-wise, there implementation on GPGPU architectures is straightforward. A kernel that handles the stream and collide procedures of the LBM algorithm is employed to compute the potential at each node of the Cartesian grid.

Returning to FIG. 2, at step 212, the simulation results are output. Simulation results may include a moving mesh that shows movement of the ventricles and a blood flow simulation. From these results, various parameters, such as ejection fraction, blood flow velocity and vorticity, stroke volume, electrophysiology parameters (ECG), regurgitations, etc., can be calculated. Since the cardiac function is modeled in near real time due to the fast GPU implementation, a user can interact with the model to simulate various cardiac therapies for a patient while in a clinical setting. The simulation results can be output by displaying computed electrophysiology potentials, biomechanical forces and cardiac parameters on a display device of a computer system. For example, one or more of the computed electrophysiology potentials, biomechanical forces, and cardiac parameters can be displayed using moving computational domains and color maps.

At step 214, user input is interactively received to change at least one of the parameters of at least one of the patient-specific anatomical model, cardiac electrophysiology model, and cardiac biomechanical model. In particular, the user may input at least one of modified biomechanical, electrophysiology, or blood flow parameters. For example modified parameters can represent various cardiac therapies or treatment options. Once the user input is received, the method returns to step 206 and recalculates the cardiac electrophysiology, cardiac biomechanics, and blood flow and cardiac movement with the modified parameters.

Figure 8:
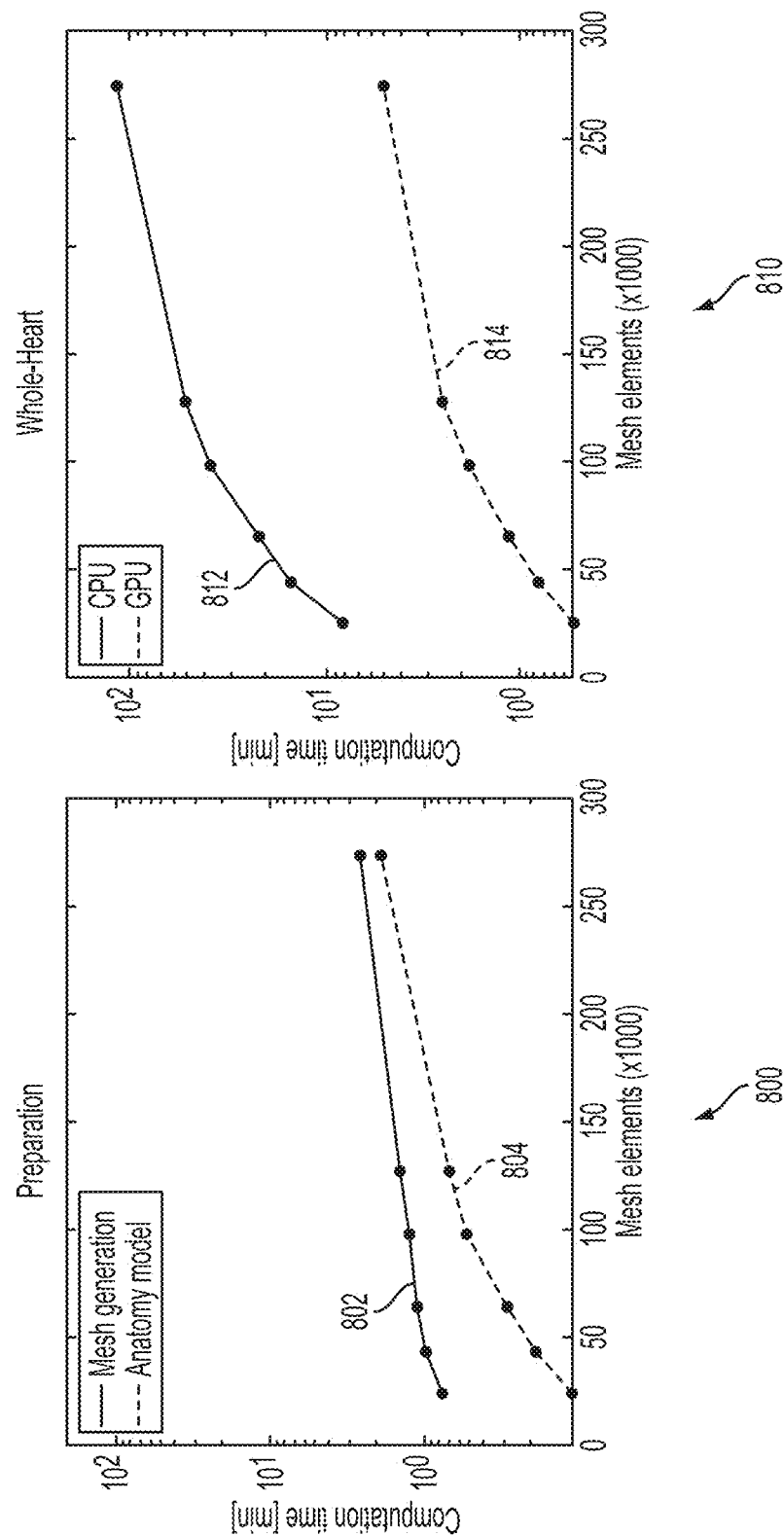
FIG. 8 illustrates benchmark results for anatomical model generation and blood flow and cardiac movement simulation with respect to meshes with various sizes generated from the same patient.

In order to assess the improvement of the above described cardiac modeling framework, the present inventors ran the entire simulation on a representative patient case with a different number of volumetric mesh elements. FIG. 8 illustrates benchmark results for meshes with various sizes generated from the same patient. In particular, FIG. 8 shows computation times for meshes with 24 k, 43 k, 64 k, 98 k, 127 k, and 274 k tetrahedra. Image 800 of FIG. 8 shows computation times for mesh generation 802 and anatomical model generation 804. Image 810 of FIG. 8 shows a comparison of computation times for CPU implementation 812 and GPU implementation 814 of whole-heart simulation. Computation times are shown in FIG. 8 using a log-scale. The time step of the Euler implicit scheme used for the simulation was set to 1 ms, and one full heart cycle of 800 ms was computed with a numerical threshold of $10^{-8}$ for the Conjugate Gradient solver. The general dynamics system parameters include a mass density of $\rho=1.07$ g/ml and Rayleigh damping coefficients of 0.05 for both mass and stiffness. The passive tissue parameters were set as in Holazapfel et al., "Constitutive Modeling of Passive Myocardium: a Structurally Based journal", *Phil. Trans. R. Soc.* 367(1902), 3445-3475 (2009) and $\sigma_0=15$ kPa. The simulation was conducted on a system with an Intel Xeon 64-bit CPU at 2.4 GHz with 16 cores, 4 GB RAM, and an NVIDIA GetForce GTX 580 graphics card.

For the anatomical model construction, detecting and tracking was performed in less than 4 seconds per frame. As shown in FIG. 5, preparation times for a mesh with median resolution (64 k) amount to 64.4 seconds for mesh generation and 16.8 seconds for anatomy model computation. The electrophysiology of the heart was calculated in an almost constant time of 2.9 to 3.2 seconds, which is not surprising as the LBM method works on a Cartesian grid with constant resolution (1.5×1.5×1.5 mm in the simulation). The most significant run-times correspond to the bio-mechanics component. Here, the simulation using the GPU implementation gained a mean speed up of 19.3 (std. dev. 2.6). For a mesh with medium resolution (64 k), the simulation only required 1 min and 9.5 seconds, and even for the mesh with the highest resolution, (274 k), an entire heart cycle could be simulated in 5 min and 2.6 seconds, still being within a clinically feasible time frame.

Figure 9:
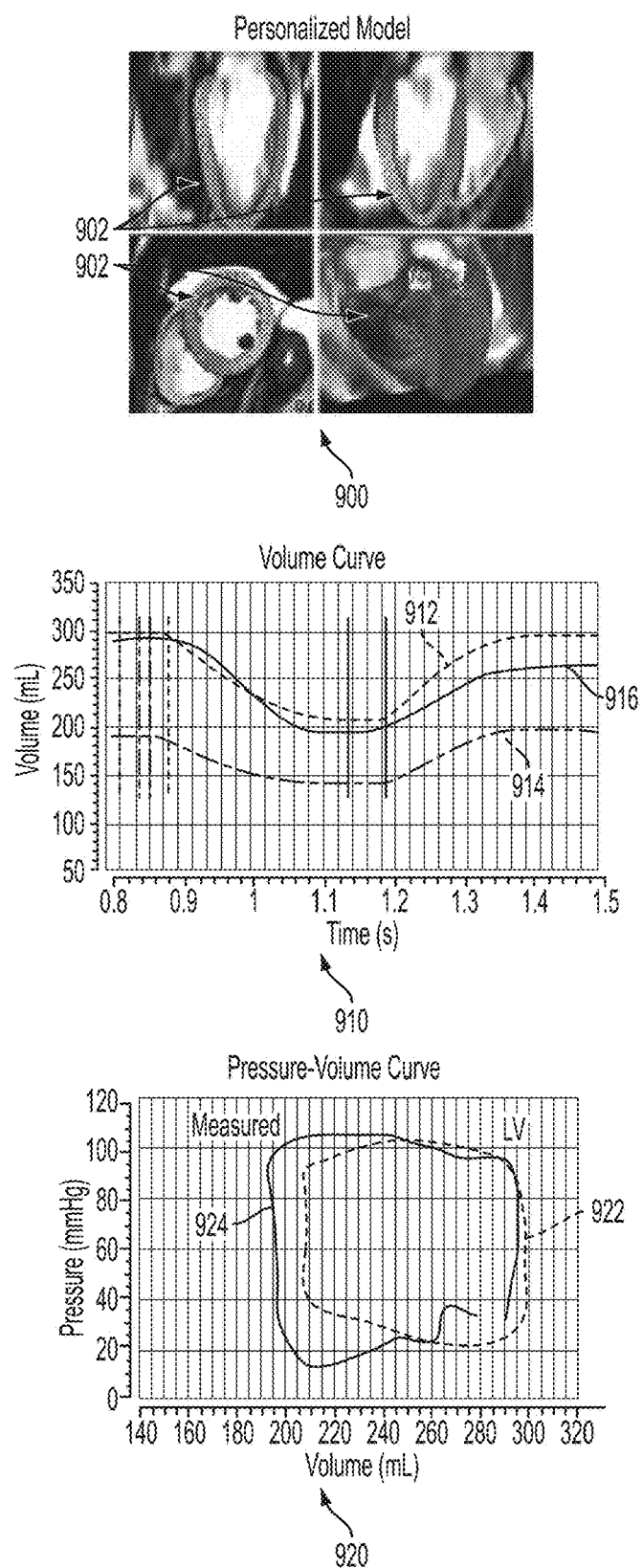
FIG. 9 illustrates the personalized model fitted to an MRI image and how it is displayed, as well as volume and pressure-volume curves computed from the model.

For the real case experiments, the present inventors used an anonymized dataset of a dilated cardiomyopathy (DCM) patient. The dataset included a cine MRI sequence and heart catheter pressure measurements of the left ventricle and aorta. The Windkessel parameters were first estimated using the aortic pressure measurements, the aortic flow obtained from the images, and the measured ejection fraction. Thereafter, the parameters of the biomechanical model and the boundary conditions were manually optimized to match the cardiac motion as shown in the images. The personalized model was successfully in modeling realistic cardiac motion and the volume-pressure curves generated by the model qualitatively represented the measured values. FIG. 9 illustrates the personalized model fitted to an MRI image, as well as volume and pressure-volume curves. As shown in FIG. 9, image 900 shows the personalized anatomical model 902 fit to an MRI image. Image 910 shows volume curves of the simulated left ventricle 912 and right ventricle 914 and the ground truth measured volume curve 916 of the left ventricle. Image 920 shows the pressure-volume curve of the left ventricle 922 resulting from the simulation and the ground truth measured pressure-volume curve 924 for the left ventricle.

In the embodiment described above, the method of FIG. 2 utilizes a Multiplicative Jacobian Energy Decomposition (MJED) framework to compute the biomechanics of the myocardium tissue in step 208. According to an alternative embodiment of the present invention, a Total Lagrangian Explicit Dynamics (TLED) method can be used instead to calculate the biomechanics in step 208. TLED is an efficient numerical algorithm for computing deformations of soft tissues such as the brain, liver, kidney, etc. Its main idea is to refer to the original, un-deformed configuration of the system to the amount of mathematical operations in each time step. This method uses an explicit integration, which implies there is no need for iterative equation solving during the time-stepping procedure. Moreover, at each time step, all calculations are node-wise. Therefore, TLED is suitable for real-time computation as it can be implemented in massively parallel architectures.

With the TLED approach, the integration of dynamic equations in time domain is done with explicit methods. As a result, treatment of non-linearities is straightforward: no iterations are required within one time step as no implicit system needs to be solved. The global system of discretized equations of motion to be solved at each time can be expressed as:

$$M\ddot{U} + D\dot{U} + K(U) = R.$$

With:

$$K(U)U = F(U) = \sum_e \tilde{F}^{(e)}$$

$${}^t\tilde{F} = \int_{{}^0V} {}^t_0 B_L^{T\,t}_0 \hat{S} \, d^0V \text{ for a given element at time } t$$

In the above equations, U is a vector of nodal displacements, M is a constant mass matrix, D is a constant damping matrix, K is a stiffness matrix non-linearly dependent on the deformation, R is a vector of external forces, $\tilde{F}^{(e)}$ are the global nodal force contributions due to stresses in elements e, ${}^t_0\hat{S}$ is the vector form of the second Piola-Kirchhoff stress, $_0^tB_L$ is the strain-displacement matrix, and $^0V$ is the initial volume of the element. The central difference integration scheme gives the time-stepping formula:

$$u_{n+1} = u_n + \Delta t_{n+1}\dot{u}_n + \tfrac{1}{2}\Delta t_{n+1}^2 \ddot{u}_n.$$

Since all displacements $^tU$ and $^{t-\Delta t}U$ for the current and previous time steps are known and all nodal forces $^tF$ have been computed, the central difference method yields the following equation for computing displacements at the next step component-wise:

$$^{t+\Delta t}U_i = A_i(^tR_i - {}^tF_i) + B_i{}^tU_i + C_i{}^{t-\Delta t}U_i,$$

With:

$$A_i = \frac{1}{\frac{D_{ii}}{2\Delta t} + \frac{M_{ii}}{\Delta t^2}} \quad B_i = \frac{2M_{ii}}{\Delta t^2}A_i \quad C_i = \frac{D_{ii}}{2\Delta t}A_i - \frac{B_i}{2}.$$

Explicit time integration operators such as the central difference method are only conditionally stable: the time step $\Delta t$ must be smaller than the critical limit $\Delta_{tcr}$. In linear elastic analyses, the following formula, can be used to automatically setup the time-step given myocardium elasticity and mesh resolution:

$$\Delta t_{cr} = \frac{L_e}{c}$$

$$c = \sqrt{\frac{E(1-v)}{\rho(1+v)(1-2v)}},$$

where $L_e$ is the smallest characteristic element length in the assembly, c is the dilatational wave speed of the material, E is the Young's modulus, vis Poisson's ratio, and $\rho$ is the density.

Figure 10:
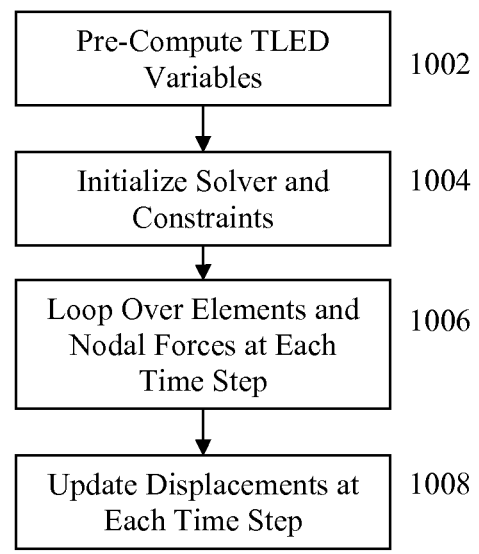
FIG. 10 illustrates a Total Lagrangian Explicit Dynamics (TLED) finite elements method for calculating cardiac biomechanics for a plurality of time steps according to an embodiment of the present invention.

FIG. 10 illustrates a TLED finite elements method for calculating cardiac biomechanics for a plurality of time steps according to an embodiment of the present invention. At step 1002, TLED variables are pre-computed. All the variables of the TLED algorithm are referred to the initial configuration with the aim to reduce the calculations in the main iteration loop. To do this, the pre-computation step of 1002 is performed to initialize those variables. The pre-computation step can be implemented as described in the following algorithm:

1. Load mesh and boundary conditions.
2. For each element compute:
   The determinant of the Jacobian det(J)
   The spatial derivatives of shape functions δh
   The linear strain-displacement matrices $_0^tB_{L0}$
3. Compute and diagonalize mass matrix $^0M$
4. Compute $A_i$, $B_i$ and $C_i$.

At step 1004, the solver and the constraints are initialized. In particular, the solver and the constraints can be initialized as follows:

1. Initialize nodal displacement $^0u=0$, $^{-\Delta t}u=0$
2. Apply load for the first time step:
   Forces: $^{\Delta t}R_t{}^{(k)} \leftarrow R^{(k)}(\Delta t)$
   Prescribed displacements: $^{\Delta t}u_t{}^{(k)} \leftarrow d(\Delta t)$.

At step 1006, at each time step, the method loops over the elements and compute their nodal forces. The calculation of the nodal forces for each of the elements can be performed as follows:

1. Take element nodal displacements from the previous time step
2. Compute deformation gradient $_0^tx$
3. Calculate full strain-displacement matrix:

$$_0^tB_L{}^{(k)} = {}_0^iB_{L00}{}^{(k)}{}^tX^T$$

This matrix accounts for initial displacement effect.
4. Compute second Piola-Kirchoff stress (vector) $_0^t\tilde{S}$ at integration points
5. Compute element nodal reaction forces $$^t\tilde{F}^{(m)} = \int_{0_V0}{}^tB_{L0}{}^{Tt}\tilde{S}d^0V$$

using Gaussian quadrature.

At step 1008, at each time step, the displacements of the nodes are updated based on the nodal forces calculated for the elements. The displacements of the nodes can be updated as follows:

1. Obtain net nodal reaction forces at time t, $^tF$.
2. Explicitly compute displacements using central difference formula:

$$^{t+\Delta t}U_i = A_i(^tR_i - {}^tF_i) + B_i{}^tU_i + C_i{}^{t-\Delta t}U_i$$

3. Apply load for the next step:
   Forces: $^{t+\Delta t}R_i{}^{(k)} \leftarrow R^{(k)}(t+\Delta t)$
   Prescribed displacements: $^{t+\Delta t}u_i{}^{(k)} \leftarrow d(t+\Delta t)$.

Figure 11:
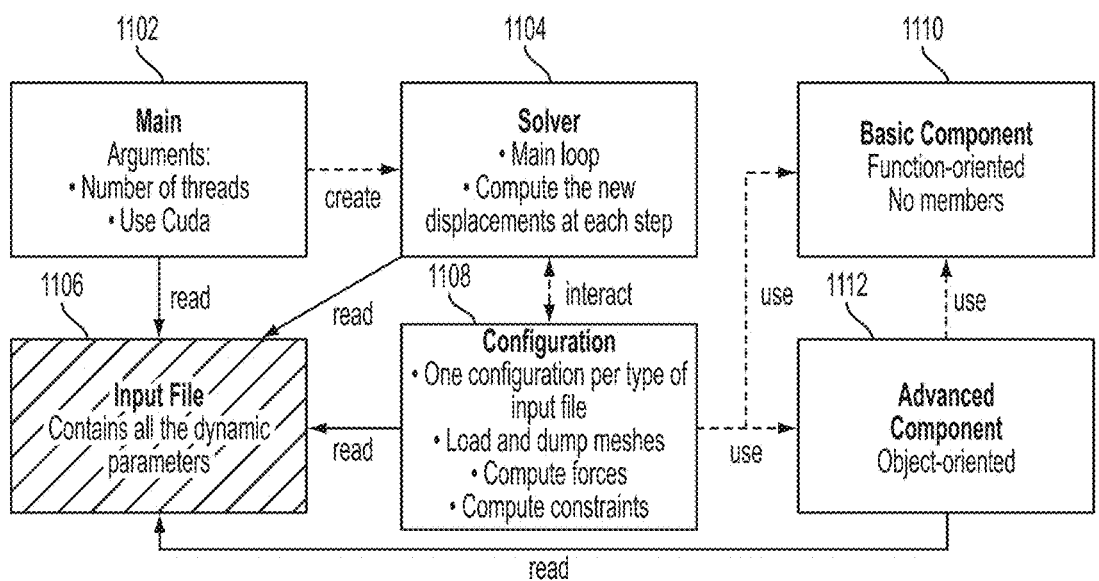
FIG. 11 illustrates a global overview of the TLED framework according to an embodiment of the present invention.

FIG. 11 illustrates a global overview of the TLED framework according to an embodiment of the present invention. To maximize performance the TLED framework can be split into two parts: a CPU, multithreaded part and a massively parallel (MP) part (e.g., NVIDIA CUDA, OpenCL, Xeon-Phi). Each component of FIG. 11 may be implemented for each part, although IO and initializations algorithms of the CPU part can be used in the MP part.

Referring to FIG. 11, the entry point of the framework 1100 is the Main component 1102, which launches the solver 1104 with the configuration described by the input file 1106. The solver 1104 performs "main loop", which is described above in the method of FIG. 10, by performing the following operations: calling the configuration method 1108 (initialization, pre-computation, step and dump related to one simulation scenario) and computing the new displacements at each time step with the central difference formula. An input file 106 is used to specify dynamic parameters, such as the number of steps, the time step, the damping coefficient, etc.

The configuration 1108 is a class (e.g., a C++ class) which loads the meshes at the initialization and computed the forces and constraints at each time step. The configuration 1108 defines the simulation scenario. For cardiac computations, the configuration 1108 defines the active stress, the pressure boundary conditions, the cardiac cycles, the pericardium and base stiffness constraints, etc. However, this framework can also be similarly utilized for other simulations scenarios, such as valve modeling, liver motion, lung motion, etc. In practice, the configuration file 1108 interacts directly with the solver 1104. Basic and advanced components 1110 and 1112, respectively, (which contain the applied forces and constraints) can be used to factorize the code between configurations.

The basic components 1110 provide basic features. These components are not able to read the input file 1106 and provide functions to maximize the framework genericity and performance. The advanced components 1112 are specific components that are not necessarily generic. The advance components 1112 are object-oriented and are able to configure themselves at the initialization with the input file 1106.

Figure 12:
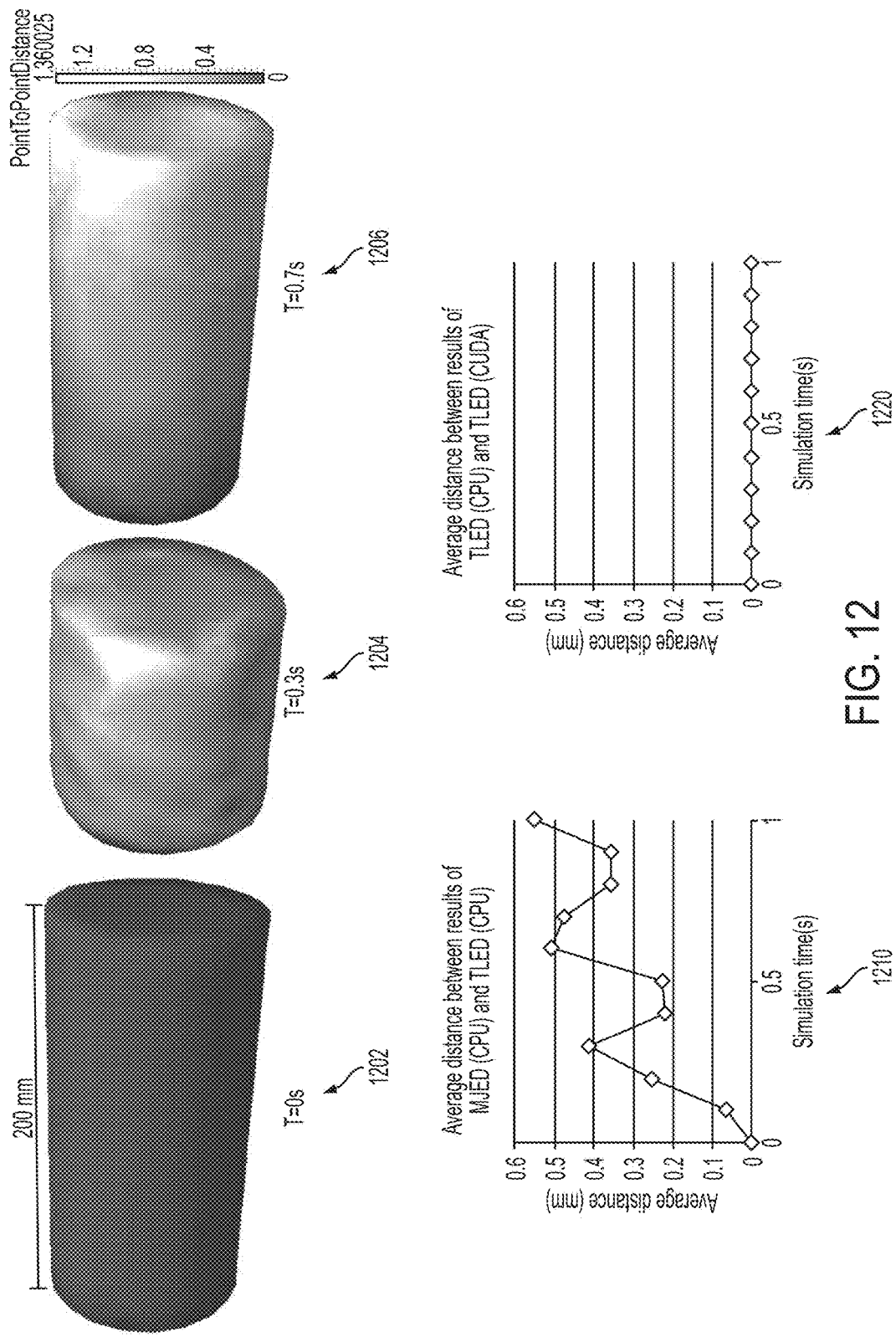
FIG. 12 illustrates exemplary results and benchmarks for the TLED framework.

FIG. 12 illustrates exemplary results and benchmarks for the TLED framework. In order the compare the accuracy of the TLED framework with the MJED framework described above, the present inventors performed a test in which a cylinder of 200×60×60 mm with heart tissue is compressed and decompressed by an active contractibility force field controlled by a pre-computed electrophysiology model. Images 1202, 1204, and 1206 show point to point distances between the MJED results and the TLED results at 0, 0.3, and 0.7 seconds, respectively. Image 1210 shows a plot of average distance between the MJED results and the TLED results over time. As can be seen, the simulated motion differs by only 0.15% of the total mesh size. Image 1220 shows difference between the CPU and MP (GPU) implementation of the TLED framework. No difference is observed between the CPU and MP (GPU) implementation of the TLED framework. This demonstrates that efficient and accurate EP models can be coupled with the TLED biomechanical framework for patient-specific heart modeling. Accordingly, the TLED framework can be coupled with the LBM-EP model of cardiac electrophysiology described above in step 206 of FIG. 2 and used to compute the cardiac biomechanics in step 208 of FIG. 2.

According to various alternative embodiments of the present invention, other material properties, such as Costa or Guccione law, can be similarly implemented in the above described cardiac modeling framework. According to various alternative embodiments of the present invention, the use of other active force models, such as the Niederer model or the Chapelle mode, can be similarly implemented in the above described cardiac modeling framework.

Embodiments of the present invention provide an integrated patient-specific framework of computational heart electromechanics that is fast enough to be applied in a clinical routine. By incorporating a very efficient LBM implementation of cardiac EP with the Holzapfel-Ogden model for passive biomechanics or the TLED framework for calculating biomechanics, the integrated framework described herein yields medically expedient results and can be applied for clinical therapy planning due to the exploitation of massively parallel GPU architectures. In an advantageous implementation, physicians are enabled to plan various DCM related surgeries, assess different surgical scenarios, and predict an intervention's outcome in silico in near real time in a clinical setting.

Figure 13:
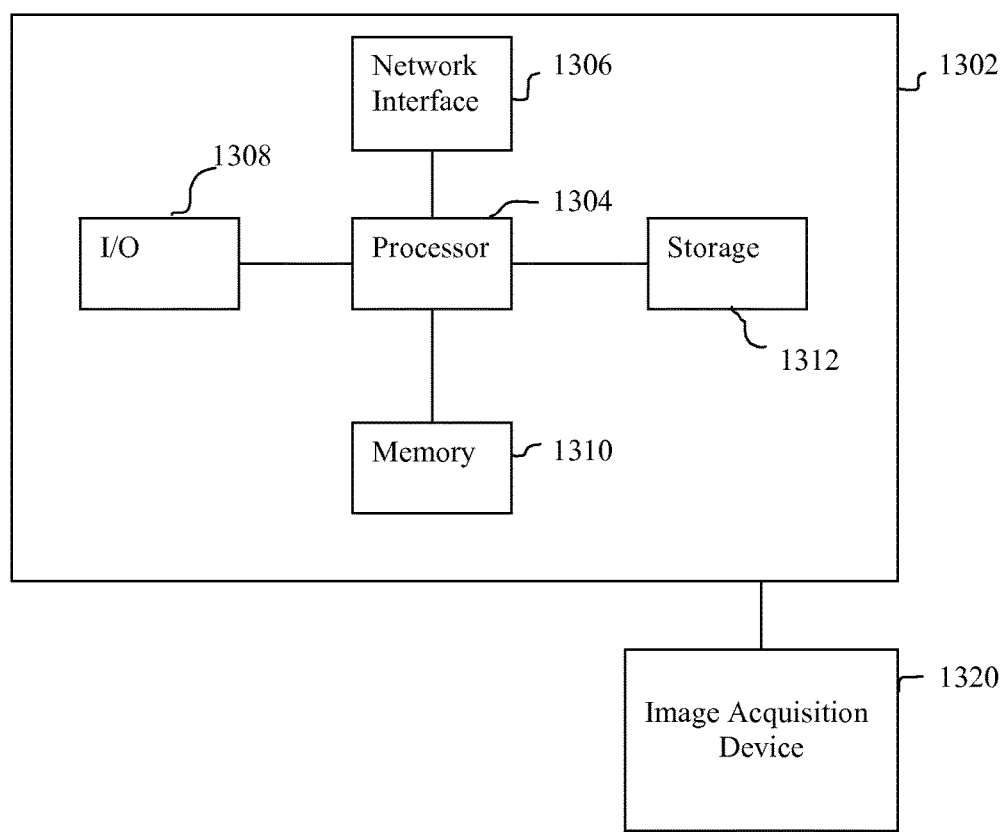
FIG. 13 is a high-level block diagram of a computer capable of implementing the present invention.

The above-described methods for patient-specific modeling and simulation of cardiac function can be implemented on a computer using well-known computer processors, memory units, storage devices, computer software, and other components. A high-level block diagram of such a computer is illustrated in FIG. 13. Computer 1302 contains a processor 1304, which controls the overall operation of the computer 1302 by executing computer program instructions which define such operation. The computer program instructions may be stored in a storage device 1312 (e.g., magnetic disk) and loaded into memory 1310 when execution of the computer program instructions is desired. Thus, the steps of the methods shown in FIGS. 1, 2, 3, 6, 10, and 11 may be defined by the computer program instructions stored in the memory 1310 and/or storage 1312 and controlled by the processor 1304 executing the computer program instructions. The processor 1304 may include a GPU, which performs specific method steps using the fast GPU implementation described above. An image acquisition device 1320, such as an MR scanning device, Ultrasound device, CT scanning device, etc., can be connected to the computer 1302 to input image data to the computer 1302. It is possible to implement the image acquisition device 1320 and the computer 1302 as one device. It is also possible that the image acquisition device 1320 and the computer 1302 communicate wirelessly through a network. The computer 1302 also includes one or more network interfaces 1306 for communicating with other devices via a network. The computer 1302 also includes other input/output devices 1308 that enable user interaction with the computer 1302 (e.g., display, keyboard, mouse, speakers, buttons, etc.). Such input/output devices 1308 may be used in conjunction with a set of computer programs as an annotation tool to annotate volumes received from the image acquisition device 1320. One skilled in the art will recognize that an implementation of an actual computer could contain other components as well, and that FIG. 13 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for interactive computation of the cardiac function of a patient, comprising:

generating a patient-specific anatomical model of at least a portion of the patient's heart from medical image data of the patient;

calculating cardiac electrophysiology potentials of the patient over a computational domain defined by the patient-specific anatomical model for each of a plurality of time steps using a patient-specific cardiac electrophysiology model, wherein for each of the plurality of time steps, the electrophysiology potentials acting on a plurality of nodes of the computational domain are calculated in parallel;

calculating biomechanical forces over the computational domain for each of the plurality of time steps using a cardiac biomechanical model coupled to the cardiac electrophysiology model, wherein for each of the plurality of time steps, the biomechanical forces acting on a plurality of nodes of the computational domain are calculated in parallel by:

pre-calculating an integer look-up table of size $2 \times N_n \times V$ that stores for each node i of the computational domain, pairs of values (j, k) corresponding to adjacent mesh elements to the node i in the computational domain, wherein j is an index of each adjacent mesh element, k is a local index of the node i for each adjacent mesh element, $N_n$ is a number of the plurality of nodes of the computational domain, and V is a maximum valence of the computational domain, and for each of the plurality of time steps:

invoking a kernel that performs element-wise calculations for each mesh element of the computational domain to compute element-wise contributions of each mesh element to the biomechanical forces acting on nodes shared by that mesh element and stores the element-wise contributions of each mesh element to the biomechanical forces acting on the nodes shared by that mesh element in floating point textures $T^k$ corresponding to respective values of the local index k of the nodes shared by that mesh element, and invoking a kernel that, for each node i of the computational domain, accumulates the element-wise contributions to the biomechanical forces acting on the node i based on the pairs of values (j, k) stored for the node i in the integer look-up table by accumulating the element-wise contributions stored at the j-th positions of the floating point textures $T^k$;

computing blood flow and cardiac movement at each of the plurality of time steps based on the calculated biomechanical forces;

displaying computed electrophysiology potentials, biomechanical forces and cardiac parameters;

receiving, interactively, user input to change at least one of the parameters of at least one of the patient-specific anatomical model, cardiac electrophysiology model, or cardiac biomechanical model; and recalculating, the electrophysiology potentials, the biomechanical forces, and the blood flow and cardiac movement.

2. The method of claim 1, wherein generating a patient-specific anatomical model of at least a portion of the patient's heart from medical image data of the patient comprises:

detecting a patient-specific left ventricle model and a patient-specific right ventricle model in the medical image data;

fusing the left ventricle model and the right ventricle model into a single bi-ventricular volumetric mesh representing the myocardium; and generating a model of fiber architecture based on the bi-ventricular mesh, wherein the model of fiber architecture includes fibers and fiber sheets.

3. The method of claim 1, wherein calculating cardiac electrophysiology potentials of the patient over a computational domain defined by the patient-specific anatomical model for each of a plurality of time steps using a patient-specific cardiac electrophysiology model comprises:

calculating an action potential at each of the plurality of nodes of the mesh domain for each of the plurality of time steps using a Lattice-Boltzmann electrophysiology method; and estimating parameters of the cardiac electrophysiology model from the medical image data and an electrocardiogram (ECG).

4. The method of claim 1, wherein the calculating cardiac electrophysiology potentials of the patient over a computational domain defined by the patient-specific anatomical model for each of a plurality of time steps using a patient-specific cardiac electrophysiology model is performed by a massively parallel architecture.

5. The method of claim 1, wherein calculating biomechanical forces over the computational domain for each of the plurality of time steps using a cardiac biomechanical model coupled to the cardiac electrophysiology model comprises:

calculating forces due to passive stress, active stress, and mechanical boundary conditions at each of the plurality of nodes of the computational domain for each of the plurality of time steps; and estimating parameters of the biomechanical model from the medical image data.

6. The method of claim 5, wherein calculating forces due to passive stress, active stress, and mechanical boundary conditions at each of the plurality of nodes of the mesh domain for each of the plurality of time steps comprises:

calculating the forces due to passive stress using a constitutive law of tissue biomechanics;

calculating the forces due to active stress based on the cardiac electrophysiology estimated using the cardiac electrophysiology model; and calculating the forces due to mechanical boundary conditions based on a first constraint corresponding to an effect of arteries and atria on ventricular motion and a second constraint corresponding to an effect of the pericardium.

7. The method of claim 1, wherein calculating biomechanical forces over the computational domain for each of the plurality of time steps using a cardiac biomechanical model coupled to the cardiac electrophysiology model comprises:

calculating the biomechanical forces over the mesh domain for each of the plurality of time steps using a Total Lagrangian Explicit Dynamics (TLED) framework.

8. The method of claim 1, wherein displaying computed electrophysiology potentials, biomechanical forces and cardiac parameters comprises:

displaying at least one of computed electrophysiology potentials, computed biomechanical forces, computed blood flow parameters and computed cardiac movement using moving computational domains and color maps.

9. The method of claim 1, wherein receiving user input to change at least one of the parameters of at least one of the patient-specific anatomical model, cardiac electrophysiology model, and cardiac biomechanical model comprises:

receiving at least one of modified biomechanical, electrophysiology, or blood flow parameters.

10. An apparatus for interactive computation of the cardiac function of a patient, comprising:

a processor; and a memory storing computer program instructions which when executed by the processor cause the processor to perform operations comprising:

generating a patient-specific anatomical model of at least a portion of the patient's heart from medical image data of the patient;

calculating cardiac electrophysiology potentials of the patient over a computational domain defined by the patient-specific anatomical model for each of a plurality of time steps using a patient-specific cardiac electrophysiology model, wherein for each of the plurality of time steps, the electrophysiology potentials acting on a plurality of nodes of the computational domain are calculated in parallel;

calculating biomechanical forces over the computational domain for each of the plurality of time steps using a cardiac biomechanical model coupled to the cardiac electrophysiology model, wherein for each of the plurality of time steps, the biomechanical forces acting on a plurality of nodes of the computational domain are calculated in parallel by:

pre-calculating an integer look-up table of size $2 \times N_n \times V$ that stores for each node i of the computational domain, pairs of values (j, k) corresponding to adjacent mesh elements to the node i in the computational domain, wherein j is an index of each adjacent mesh element, k is a local index of the node i for each adjacent mesh element, $N_n$ is a number of the plurality of nodes of the computational domain, and V is a maximum valence of the computational domain, and for each of the plurality of time steps:
invoking a kernel that performs element-wise calculations for each mesh element of the computational domain to compute element-wise contributions of each mesh element to the biomechanical forces acting on nodes shared by that mesh element and stores the element-wise contributions of each mesh element to the biomechanical forces acting on the nodes shared by that mesh element in floating point textures $T^k$ corresponding to respective values of the local index k of the nodes shared by that mesh element, and invoking a kernel that, for each node i of the computational domain, accumulates the element-wise contributions to the biomechanical forces acting on the node i based on the pairs of values (j, k) stored for the node i in the integer look-up table by accumulating the element-wise contributions stored at the j-th positions of the floating point textures $T^k$;

computing blood flow and cardiac movement at each of the plurality of time steps based on the calculated biomechanical forces;

displaying computed electrophysiology potentials, biomechanical forces and cardiac parameters;

receiving, interactively, user input to change at least one of the parameters of at least one of the patient-specific anatomical model, cardiac electrophysiology model, or cardiac biomechanical model; and recalculating, the electrophysiology potentials, the biomechanical forces, and the blood flow and cardiac movement.

11. The apparatus of claim 10, wherein generating a patient-specific anatomical model of at least a portion of the patient's heart from medical image data of the patient comprises:
detecting a patient-specific left ventricle model and a patient-specific right ventricle model in the medical image data;
fusing the left ventricle model and the right ventricle model into a single bi-ventricular volumetric mesh representing the myocardium; and
generating a model of fiber architecture based on the bi-ventricular mesh, wherein the model of fiber architecture includes fibers and fiber sheets.

12. The apparatus of claim 10, wherein calculating cardiac electrophysiology potentials of the patient over a computational domain defined by the patient-specific anatomical model for each of a plurality of time steps using a patient-specific cardiac electrophysiology model comprises:
calculating an action potential at each of the plurality of nodes of the mesh domain for each of the plurality of time steps using a Lattice-Boltzmann electrophysiology method; and
estimating parameters of the cardiac electrophysiology model from the medical image data and an electrocardiogram (ECG).

13. The apparatus of claim 10, wherein calculating biomechanical forces over the computational domain for each of the plurality of time steps using a cardiac biomechanical model coupled to the cardiac electrophysiology model comprises:
calculating forces due to passive stress, active stress, and mechanical boundary conditions at each of the plurality of nodes of the computational domain for each of the plurality of time steps; and
estimating parameters of the biomechanical model from the medical image data.

14. The apparatus of claim 13, wherein calculating forces due to passive stress, active stress, and mechanical boundary conditions at each of the plurality of nodes of the mesh domain for each of the plurality of time steps comprises:
calculating the forces due to passive stress using a constitutive law of tissue biomechanics;
calculating the forces due to active stress based on the cardiac electrophysiology estimated using the cardiac electrophysiology model; and
calculating the forces due to mechanical boundary conditions based on a first constraint corresponding to an effect of arteries and atria on ventricular motion and a second constraint corresponding to an effect of the pericardium.

15. The apparatus of claim 10, wherein calculating biomechanical forces over the computational domain for each of the plurality of time steps using a cardiac biomechanical model coupled to the cardiac electrophysiology model comprises:
calculating the biomechanical forces over the mesh domain for each of the plurality of time steps using a Total Lagrangian Explicit Dynamics (TLED) framework.

16. The apparatus of claim 10, wherein displaying computed electrophysiology potentials, biomechanical forces and cardiac parameters comprises:
displaying at least one of computed electrophysiology potentials, computed biomechanical forces, computed blood flow parameters and computed cardiac movement using moving computational domains and color maps.

17. The apparatus of claim 10, wherein receiving user input to change at least one of the parameters of at least one of the patient-specific anatomical model, cardiac electrophysiology model, and cardiac biomechanical model comprises:
receiving at least one of modified biomechanical, electrophysiology, or blood flow parameters.

18. A non-transitory computer readable medium storing computer program instructions for interactive computation of the cardiac function of a patient, the computer program instructions when executed on a processor cause the processor to perform operations comprising:
generating a patient-specific anatomical model of at least a portion of the patient's heart from medical image data of the patient;
calculating cardiac electrophysiology potentials of the patient over a computational domain defined by the patient-specific anatomical model for each of a plurality of time steps using a patient-specific cardiac electrophysiology model, wherein for each of the plurality of time steps, the electrophysiology potentials acting on a plurality of nodes of the computational domain are calculated in parallel;
calculating biomechanical forces over the computational domain for each of the plurality of time steps using a cardiac biomechanical model coupled to the cardiac electrophysiology model, wherein for each of the plurality of time steps, the biomechanical forces acting on a plurality of nodes of the computational domain are calculated in parallel by:

pre-calculating an integer look-up table of size $2 \times N_n \times V$ that stores for each node i of the computational domain, pairs of values (j, k) corresponding to adjacent mesh elements to the node i in the computational domain, wherein j is an index of each adjacent mesh element, k is a local index of the node i for each adjacent mesh element, $N_n$ is a number of the plurality of nodes of the computational domain, and V is a maximum valence of the computational domain, and for each of the plurality of time steps:

invoking a kernel that performs element-wise calculations for each mesh element of the computational domain to compute element-wise contributions of each mesh element to the biomechanical forces acting on nodes shared by that mesh element and stores the element-wise contributions of each mesh element to the biomechanical forces acting on the nodes shared by that mesh element in floating point textures $T^k$ corresponding to respective values of the local index k of the nodes shared by that mesh element, and invoking a kernel that, for each node i of the computational domain, accumulates the element-wise contributions to the biomechanical forces acting on the node i based on the pairs of values (j, k) stored for the node i in the integer look-up table by accumulating the element-wise contributions stored at the j-th positions of the floating point textures $T^k$;

computing blood flow and cardiac movement at each of the plurality of time steps based on the calculated biomechanical forces;

displaying computed electrophysiology potentials, biomechanical forces and cardiac parameters;

receiving, interactively, user input to change at least one of the parameters of at least one of the patient-specific anatomical model, cardiac electrophysiology model, or cardiac biomechanical model; and recalculating, the electrophysiology potentials, the biomechanical forces, and the blood flow and cardiac movement.

19. The non-transitory computer readable medium of claim 18, wherein generating a patient-specific anatomical model of at least a portion of the patient's heart from medical image data of the patient comprises:

detecting a patient-specific left ventricle model and a patient-specific right ventricle model in the medical image data;

fusing the left ventricle model and the right ventricle model into a single bi-ventricular volumetric mesh representing the myocardium; and generating a model of fiber architecture based on the bi-ventricular mesh, wherein the model of fiber architecture includes fibers and fiber sheets.

20. The non-transitory computer readable medium of claim 18, wherein calculating cardiac electrophysiology potentials of the patient over a computational domain defined by the patient-specific anatomical model for each of a plurality of time steps using a patient-specific cardiac electrophysiology model comprises:

calculating an action potential at each of the plurality of nodes of the mesh domain for each of the plurality of time steps using a Lattice-Boltzmann electrophysiology method; and estimating parameters of the cardiac electrophysiology model from the medical image data and an electrocardiogram (ECG).

21. The non-transitory computer readable medium of claim 18, wherein the calculating cardiac electrophysiology potentials of the patient over a computational domain defined by the patient-specific anatomical model for each of a plurality of time steps using a patient-specific cardiac electrophysiology model is performed by a massively parallel architecture.

22. The non-transitory computer readable medium of claim 18, wherein calculating biomechanical forces over the computational domain for each of the plurality of time steps using a cardiac biomechanical model coupled to the cardiac electrophysiology model comprises:

calculating forces due to passive stress, active stress, and mechanical boundary conditions at each of the plurality of nodes of the computational domain for each of the plurality of time steps; and estimating parameters of the biomechanical model from the medical image data.

23. The non-transitory computer readable medium of claim 22, wherein calculating forces due to passive stress, active stress, and mechanical boundary conditions at each of the plurality of nodes of the mesh domain for each of the plurality of time steps comprises:

calculating the forces due to passive stress using a constitutive law of tissue biomechanics;

calculating the forces due to active stress based on the cardiac electrophysiology estimated using the cardiac electrophysiology model; and calculating the forces due to mechanical boundary conditions based on a first constraint corresponding to an effect of arteries and atria on ventricular motion and a second constraint corresponding to an effect of the pericardium.

24. The non-transitory computer readable medium of claim 18, wherein calculating biomechanical forces over the computational domain for each of the plurality of time steps using a cardiac biomechanical model coupled to the cardiac electrophysiology model comprises:

calculating the biomechanical forces over the mesh domain for each of the plurality of time steps using a Total Lagrangian Explicit Dynamics (TLED) framework.

25. The non-transitory computer readable medium of claim 18, wherein displaying computed electrophysiology potentials, biomechanical forces and cardiac parameters comprises:

displaying at least one of computed electrophysiology potentials, computed biomechanical forces, computed blood flow parameters and computed cardiac movement using moving computational domains and color maps.

26. The non-transitory computer readable medium of claim 18, wherein receiving user input to change at least one of the parameters of at least one of the patient-specific anatomical model, cardiac electrophysiology model, and cardiac biomechanical model comprises:

receiving at least one of modified biomechanical, electrophysiology, or blood flow parameters.

* * * * *